United States Patent [19]

Muraoka et al.

[11] Patent Number: 4,750,812
[45] Date of Patent: Jun. 14, 1988

[54] OBJECTIVE OBSERVATION OPTICAL MATERIAL

[75] Inventors: Koji Muraoka, Sabae; Fumiki Tatibana; Katsuhiko Nakatsuka, both of Fukui; Hiroyuki Niwa, Sabae; Tadahiro Yamatani, Fukui, all of Japan

[73] Assignee: Kabushika Kaisha Shuho, Fukui, Japan

[21] Appl. No.: 820,937

[22] Filed: Jan. 21, 1986

[30] Foreign Application Priority Data

Jan. 24, 1985 [JP] Japan .................................. 60-9849
Feb. 15, 1985 [JP] Japan ................................ 60-26473
Feb. 28, 1985 [JP] Japan ............................ 60-27244[U]

[51] Int. Cl.⁴ ...................... G02B 27/02; G02C 7/16
[52] U.S. Cl. ................................ 350/319; 350/276 R; 351/46
[58] Field of Search ................... 350/319, 322, 276 R; 351/44–46; 206/294, 485; 283/105; 281/29, 42, 50; 224/164

[56] References Cited

U.S. PATENT DOCUMENTS 2,230,009  1/1941  Ordoriea .
3,731,993  5/1973  Peringer .
3,794,414  2/1974  Wesley .................................. 351/46
3,967,885  7/1976  Byler .................................... 351/46
4,012,129  3/1977  Byler .................................... 351/46
4,249,803  2/1981  Byler .................................... 351/46

FOREIGN PATENT DOCUMENTS 755442   12/1971  Belgium .
0141736   5/1985  European Pat. Off. .
372473    6/1907  France ................................. 351/46
489442    7/1938  United Kingdom ................. 351/44
1026839   4/1966  United Kingdom .

Primary Examiner—John K. Corbin
Assistant Examiner—Loha Ben
Attorney, Agent, or Firm—Thomas H. Whaley

[57] ABSTRACT

An objective observation optical material comprises a sheet material composed of a plurality of spot-like transparent portions and an opaque portion and each of the spot-like transparent portions is formed into a circular shape having preferably a diameter of 0.7 to 2.0 mm or substantially a polygonal shape (including one whose sides are curved arcuately) inscribing or circumscribing such circle. The spot-like transparent portions are arranged to scatter in uniformly arranged positions so as to form connected regular triangles or squares whose sides are for example in the range from 2.0 to 5.5 mm.

13 Claims, 4 Drawing Sheets

FIG. 1
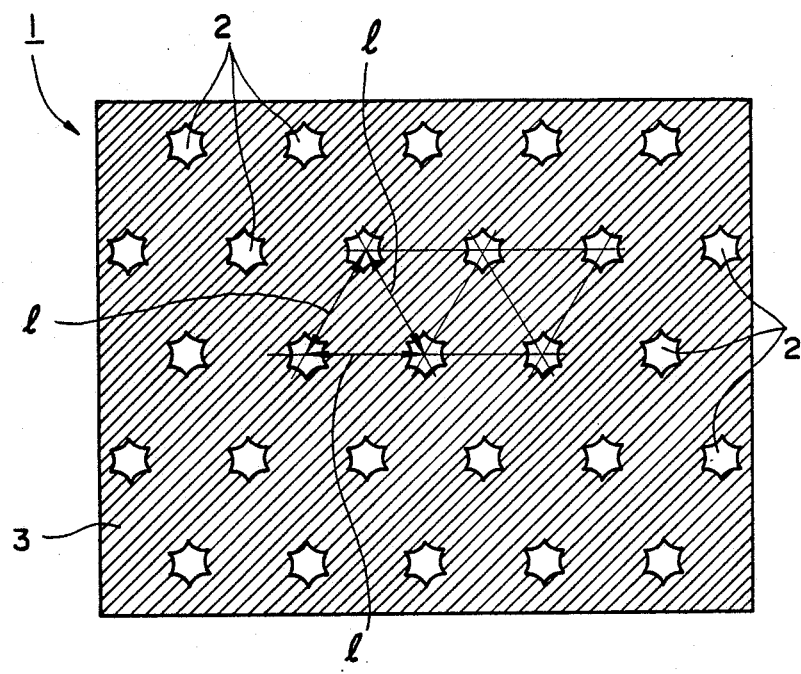
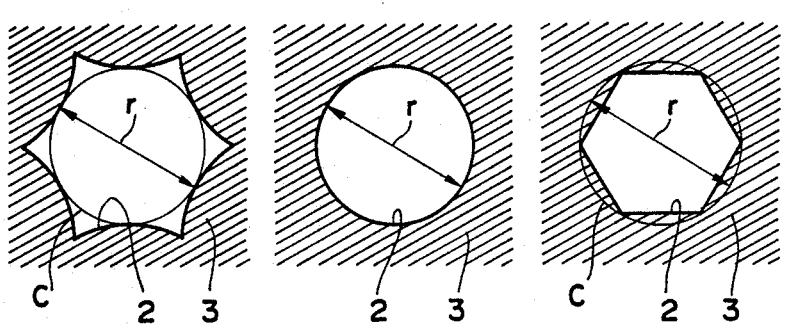
FIG. 2A  FIG. 2B  FIG. 2C

OBJECTIVE OBSERVATION OPTICAL MATERIAL

BACKGROUND OF THE INVENTION

1. Field of the Invention

The present invention relates to an objective oberservation optical material capable of screening ultraviolet rays and correcting such defects of vision as nearsightedness, farsightedness, astigmatism and presbyopia.

2. Description of the Prior Art

In the past, generally the incidence of ultraviolet rays to the eyes has been prevented by the use of glasses made by providing parallel-surface glasses or plastic pieces with suitable light screening properties and/or absorbing properties with respect to specific wavelengths by adding a light screening or absorbing substance during their raw material stage, coloring the transparent glasses or applying a coating to the surface of the glasses, i.e., so-called sunglasses and in the case of the wearer having nearsightedness, farsightedness, astigmatism or presbyopia the glasses have consisted of lenses or other glasses have been worn on the sunglasses for correcting the defect of vision.

However, such sunglasses are expensive and often they are not used habitually thus requiring the provision of a case for carrying or accommodating the glasses. Also, in everyday life or when going out, particulary or for protection from the intense sunshine in the summer, the sunshine on a snowy day or the reflected light of such sunshine, it is necessary to use a more powerful ultraviolet screening substitute for glasses in place of the sunglasses and the same applies to any person having nearsightedness farsightedness, astigmatism or presbyopia.

SUMMARY OF THE INVENTION

It is the primary object of the present invention to provide an objective observation optical material which is so designed that where such a situation occurs in a moment and sunglasses and correction glasses are not on hand but a person is required to look at a thing, it is possible to use the material for providing in place of such glasses any of those things kept at one's side or carried on the person, e.g., a stationery such as an underlaying sheet or ruler, a book cover, a bookmarker, a corner of a book cover, a cash card, credit card or member's card, a watch band, a shoulder belt for bags or a tag.

In other words, in accordance with the invention the objective observation optical material comprises an opaque sheet formed with a large number of uniformly scattered spot-like transparent portions and each of the spot-like transparent portions is formed into a circular shape having a diameter in the range of 0.7 to 2.0 mm or substantially a polygonal shape inscribing or circumscribing this circle (including one whose sides are each curved arcuately). The transparent portions should preferably be scattered uniformly in a staggered manner, for example, so that their center distance becomes 2.0 to 5.5 mm. Suitable materials for the above-constructed optical material of this invention must be substances having a suitable strength, physical properties, elegance and durability required for use as the materials for the previously mentioned articles as well as the capacity for maintaining the transparency of the transparent portions for a comparatively long period of time and these substances include for example plastics such as soft or hard polyvinyl chloride, polyacrylic, methacrylic acid, polyurethane, polyolefin and polyester plastics. It is to be noted that the transparent portions may take the form of holes made through the material and the material may be an opaque material such as a metal sheet. There is no particular need to limit the material to the above-mentioned plastics.

On the other hand, means for forming the spot-like transparent portions and the opaque portion separately from each other may be a method in which an opaque portion is printed by photogravure on the surface of a transparent sheet of such plastic material so as to leave spot-like blank portions and then a transparent film is applied onto the printed surface or it may be a method of printing an opaque layer over the whole surface of a transparent film and forming transparent portions or holes by such means as etching or punching. Also, any of various other methods may be used.

The thus constructed objective observation optical material of this invention is used daily in conformity with the purpose for which the article is primarily intended so that when a need occurs in a moment to confirm an object in a place where ultraviolet rays are abundant irrespective of indoor or outdoor, the optical material is held in front of the eyes to face and look at the object or view a field. In such a case, the amount of the incident light to the eyes through the spot-like transparent portions is restricted considerably by the opaque portion and one may gaze or stare at the object with open eyes. As a result, the eyes unconsciously make movements to distinguish the object in sight so that the ciliary body or the structure for adjusting the curvature of the crystalline lens in front of the eyeball of each eye functions naturally in such a manner that the curvature is decreased if the person is nearsighted and the curvature is increased if the person is farsighted thereby permitting detailed observation of the object.

Thus, not only a person of the normal vision but also a person having nearsightedness, farsightedness, astigmatism or presbyopia can comparatively accurately look at an object through the optical material according to the invention.

This principle is similar to that of a pinhole camera which takes a picture through a minute aperture so that even if there are variations in the relative distance of an object corresponding to the object to be photographed in the case of a camera, the focal point is not varied much owing to the long depth of focus and therefore the object can be seen clearly through the optical material.

The above and other objects as well as advantageous features of the invention will become more clear from the following description taken in conjunction with the drawings.

BRIEF DESCRIPTION OF THE DRAWINGS

FIG. 1 is a partial plan view showing in enlarged form an embodiment of an optical material according to the invention.

FIGS. 2A, 2B and 2C show some exemplary geometrical shapes of the spot-like transparent portions.

DESCRIPTION OF THE PREFERRED EMBODIMENTS

Referring to FIGS. 1, 2A, 2B and 2C, numeral 1 designates an optical material according to the invention, and 2 a plurality of spot-like transparent portions formed into a polygonal shape such as one whose sides circumscribe a circle of a diameter r and are arcuately curved as shown in FIG. 2A, a circular shape of a diameter r as shown in FIG. 2B or a polygonal shape inscribing a circle of a diameter r as shown in FIG. 2C. A plurality of such spot-like transparent portions 2 are each arranged at the apex of each of a plurality of contiguous regular triangles whose sides have a length of 2.0 to 5.5 mm as shown at 1 in FIG. 1 and thus the transparent portions 2 are arranged in a staggered manner. Numeral 3 designates an opaque portion. FIGS. 2A and 2C show the hexagonal transparent portions and in FIG. 2A the sides of the hexagonal shape are curved inwardly.

Figure 3:
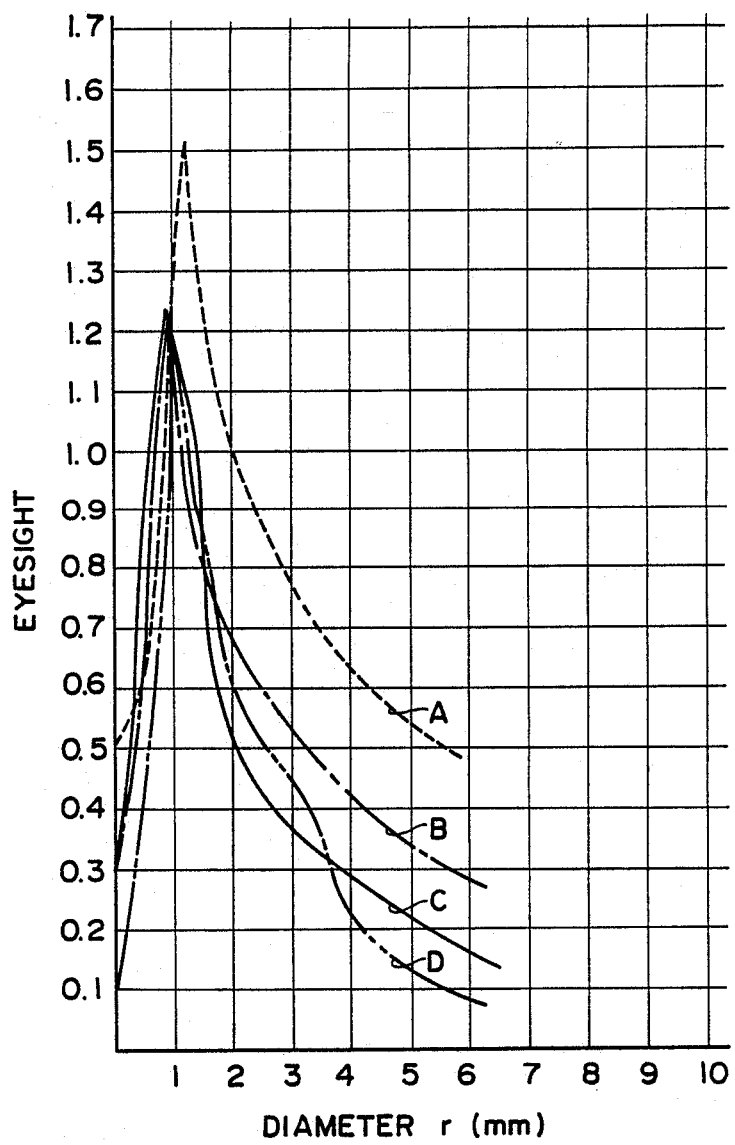
FIG. 3 is a graph showing the relation between the hole diameter and the eyesight (directional eyesight or the definition of an object viewed through the holes formed in the optical material of FIG. 1.

Referring to FIG. 3, there is illustrated a graph showing the relation between the diameter r of the spot-like transparent portions 2 and the eyesight (directional eyesight) when looking at an object by using the optical material according to the embodiment of FIG. 1. From this Figure it will be seen that an essential requirement of the invention resides in that the diameter r of the plurality of spot-like transparent portions is selected between 0.7 and 2.0 mm and preferably between 1.0 and 1.2 mm.

It is to be noted that the spot-like transparent portions may take the form of spot-like holes formed through the material and it has been confirmed that from the standpoint of reducing the interference in the field of view it is preferable to arrange the transparent portions 2 uniformly at such positions that their center distance becomes 3.0 and 5.0 mm, that is, they are arranged to scatter in a staggered manner so as to form regular triangles or squares whose sides are between 2.0 and 5.5 mm.

While it is more desirable to use a plastic material for forming the optical material 1 in the light of physical properties, working properties in manufacture, cost and elegancy as mentioned previously, the invention is not necessarily limited to such plastic materials and the use of materials having the same effects is of course within the scope of the invention. Also, while a description has been made of suitable means for forming the holes or transparent portions 2 and the opaque portion 3, the invention is not limited to these means and a metal sputtering employing a mask and the like may also be used as effective means for the purpose.

From the foregoing description it will be seen that in addition to an essential application of an article made by using as its material the optical material of the invention, e.g., an underlaying sheet, ruler, book cover, corner of a book cover, part of a bookmarker, cash card, member's card, commutation ticket holder, watch band, shoulder belt for bags or tag, the optical material of this invention is not only effective for use as an objective observation optical material in place of sunglasses when its use is required to protect the user from the glare of ultraviolet rays such as the intense sunlight or the reflection from deep snows but also effective to correct such defect of vision as the nearsightedness, farsightedness, astigmatism or presbyopia. These effects are attained by the fact that the shape and size (area) of the plurality of spot-like transparent portions 2 as well as their positions in the opaque portion 3 are specified such that the adjacent transparent portions overlap in the field of view and there is no break in the field of view thereby providing the continuous field of view. On the other hand, a greater part of the ultraviolet rays to the field of view is blocked by the opaque portion 3 and also the field of view is continuous as mentioned previously. Thus, there is no obstruction from the vision point of view thus permitting to accurately look at an object in the intense ultraviolet rays.

Figure 4:
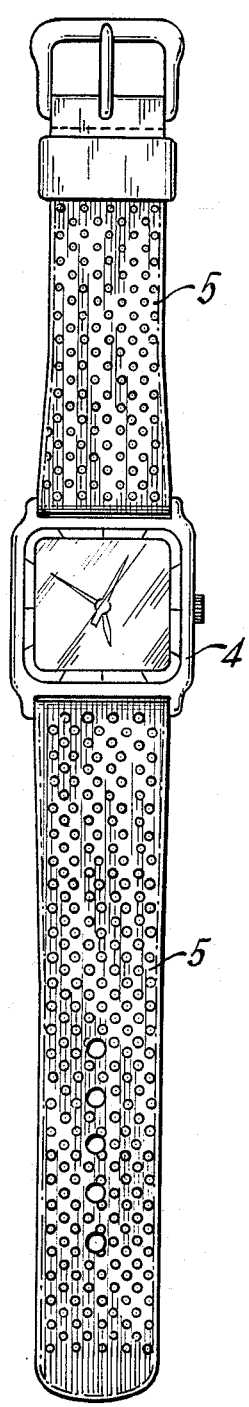
FIG. 4 is a plan view of a watch band made of the optical material shown in FIG. 1.

FIG. 4 shows by way of example a watch band made of the optical material 1 shown in FIG. 1. In the Figure, numeral 4 designates the watch proper and 5 the band made of the optical material.

Figure 5:
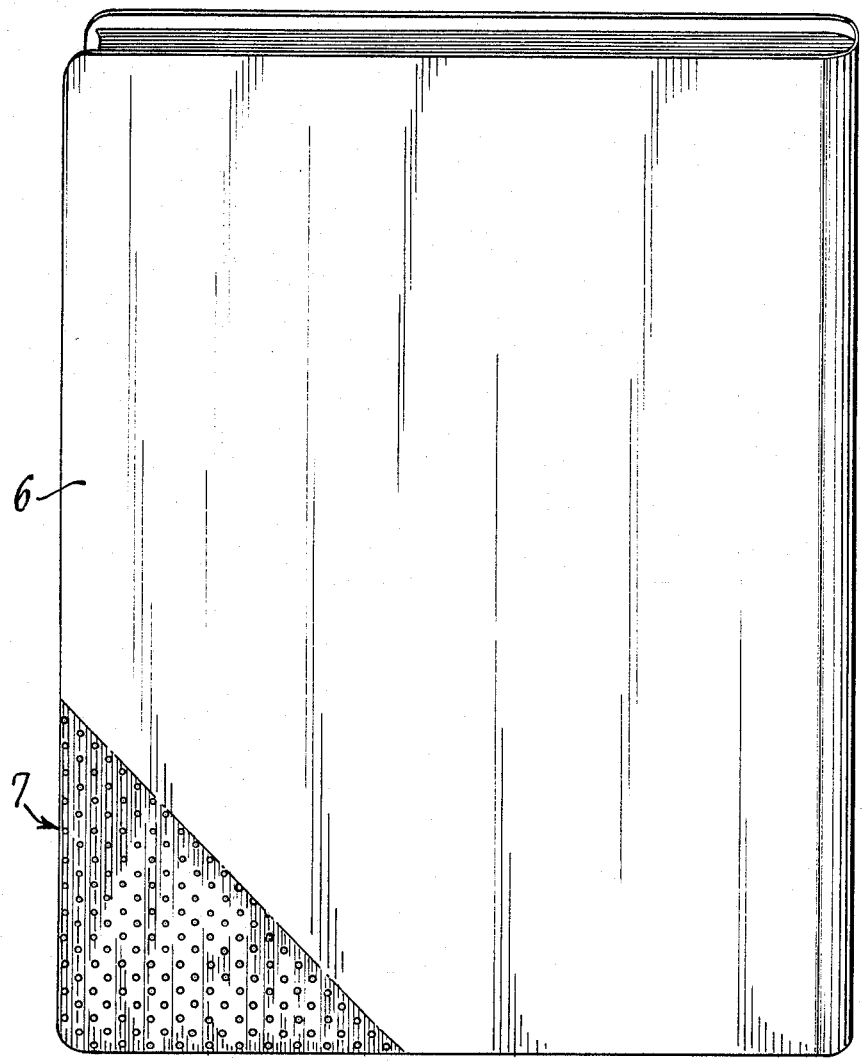
FIG. 5 is a plan view of a book cover incorporating in corner thereof the optical material shown in FIG. 1.

FIG. 5 shows an exemplary application in which the optical material 1 of FIG. 1 is incorporated in a portion 7 of a cover of a book cover 6 and the portion 7 is cut off the cover to read the book through it in place of glasses for far vision.

Figure 6:
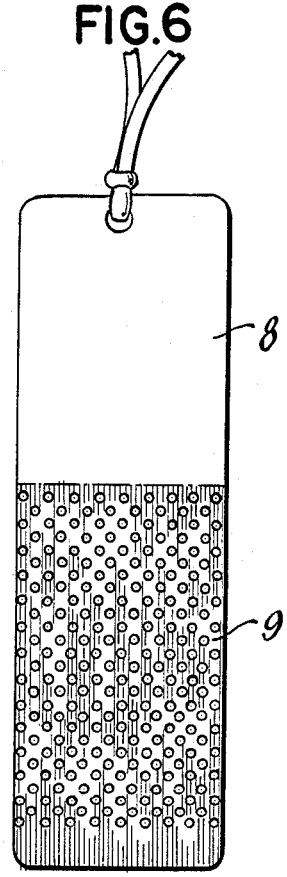
FIG. 6 is a plan view of a bookmarker incorporating in a part thereof the optical material shown in FIG. 1

FIG. 6 also shows an exemplary application in which the optical material 1 of FIG. 1 is incorporated in a bookmarker 8 and a portion 9 of the bookmarker 8 is made of the optical material 1.

Figure 7:
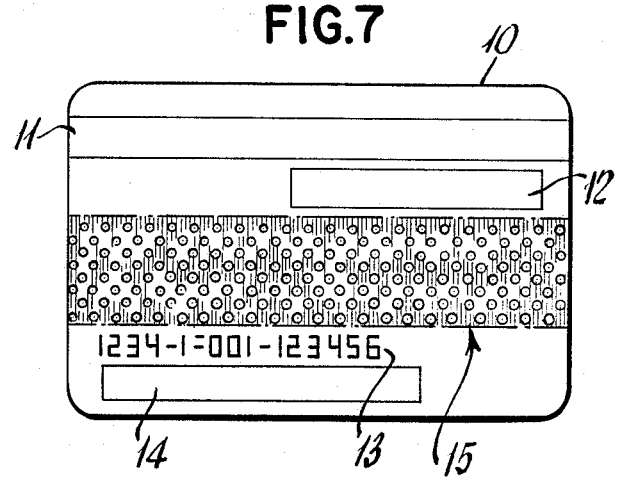
FIG. 7 shows an example in which the optical material of FIG. 1 is incorporated in a cash card.

FIG. 7 shows another exemplary application in which the optical material of the invention is incorporated in a bank cash card. In the Figure, numeral 10 designates a card, 11 a magnetic recording zone, 12 a bank name stamping portion, 13 a registration number stamping portion, 14 a depositor's name stamping portion, and 15 scattering arranged spot-like transparent portions arranged in a centralized area of the card.

We claim:

1. An optical objective sheet material which is capable of permitting sufficient light transmission therethrough to support human vision, at least a part of the sheet being generally opaque but with a large number of spot-like transparent portions distributed uniformly thereover, each spot-like transparent portion being formed of substantially hexagonal shape inscribing a circle having a diameter in the range of 0.7 to 2.0 mm, the sides of the hexagonal shape being arcuately concaved and the transparent portions arranged in a staggered manner such that lines connecting their adjacent central points form regular triangles.

2. An optical material as claimed in claim 1 wherein the centers of adjacent transparent portions are spaced at distances in the range from 2 to 5.5 mm.

3. An optical material as claimed in claim 1 wherein the centers of adjacent transparent portions are uniformly spaced from one another at a distance in the range of 3 to 5 mm.

4. An optical material as claimed in claim 1, wherein each spot-like transparent portion comprises a hole formed through the sheet material.

5. A dual function assembly device comprising a readily portable and/or accessible object having, as a part of it, or associated with it, another object having a primary function, and also as a part of it, or associated with it, a piece of sheet material at least a portion of which has a secondary function of forming an optical objective which is capable of permitting sufficient light transmission therethrough to support human vision, at least a part of the sheet being generally opaque but with a large number of spot-like transparent portions distributed uniformly thereover, each spot-like transparent portion being formed of substantially hexagonal shape inscribing a circle having a diameter in the range of 0.7 to 2.0 mm, the sides of the hexagonal shape being arcuately concaved and the transparent portions arranged in a staggered manner such that lines connecting their adjacent central points form regular triangles.

6. A device according to claim 5 wherein said device is a wrist watch band comprising said sheet material.

7. A device according to claim 5 wherein said sheet material forms a part of a book cover.

8. A device according to claim 2 wherein said spot-like transparent portions of said sheet material are confined to one corner of a book cover.

9. A device according to claim 5 wherein said sheet material comprises a bookmark.

10. A device according to claim 9 wherein said spot-like transparent portions are confined to an area no more than half the area of the bookmark.

11. A device according to claim 5 wherein said sheet material comprises a credit card or cash card.

12. A device according to claim 11 wherein said spot-like transparent portions are confined to a centralized area of said card.

13. A dual function device according to claim 5 wherein the centers of adjacent transparent portions are uniformly spaced from one another at a distance in the range of from 2 to 5 mm.

* * * * *